United States Patent [19]

Eppler et al.

[11] Patent Number: 4,970,000

[45] Date of Patent: Nov. 13, 1990

[54] METHOD FOR THE BIOLOGICAL DENITRIFICATION OF WATER

[76] Inventors: Dieter Eppler; Alwin Eppler, both of Gartenstrasse 9, D 7295 Dornstetten, Fed. Rep. of Germany

[21] Appl. No.: 393,042

[22] Filed: Aug. 8, 1989

Related U.S. Application Data

[63] Continuation of Ser. No. 912,545, Sep. 29, 1986, abandoned.

[30] Foreign Application Priority Data

Sep. 28, 1985 [DE] Fed. Rep. of Germany ....... 3534716

[51] Int. Cl.$^5$ .............................................. C02F 3/34
[52] U.S. Cl. ................................... 210/605; 210/611; 210/618; 210/631; 210/903
[58] Field of Search ............... 210/605, 610, 611, 617, 210/618, 630, 150, 151, 188, 292, 293, 903; 435/262

[56] References Cited

U.S. PATENT DOCUMENTS

| | | |
|---|---|---|
| 409,099 | 8/1889 | Griscom . |
| 3,617,540 | 11/1971 | Bishop et al. ........................ 210/903 |
| 3,642,205 | 2/1972 | Marty .................................. 210/293 |
| 3,829,377 | 8/1974 | Hashimoto ........................... 210/11 |
| 3,846,289 | 11/1974 | Jeris et al. ........................... 210/903 |
| 4,017,276 | 4/1977 | Bloem ................................. 55/53 |
| 4,056,465 | 11/1977 | Spector ................................ 210/605 |
| 4,177,144 | 12/1979 | Hickey et al. ....................... 210/293 |
| 4,469,599 | 9/1984 | Gros et al. .......................... 210/903 |
| 4,604,197 | 8/1986 | Louboutin et al. ................. 210/293 |
| 4,696,747 | 9/1987 | Verstraete et al. ................. 210/903 |

FOREIGN PATENT DOCUMENTS

| | | | |
|---|---|---|---|
| 2337576 | 8/1977 | France ................................ 210/903 |
| 53-89259 | 8/1978 | Japan .................................. 210/903 |

OTHER PUBLICATIONS

Ginocchio, J. C.; "Biological Denitrification of Drinking Water"; Subzer Technical Review; pp. 115-117 (3/1980).

Betz, Handbook of Industrial Water Conditioning, 7th Edition; pp. 81-85 (1976).

Appl. Microbiol. Biotechnol (1985) 23:152-155, Jack T. Trevors; The Influence of Oxygen Concentrations . . .

Journal WPCF, vol. 48, No. 7, Jul. 1976, pp. 1840 to 1842, Denitrification of Wastewater Effluents with Methane.

Toxicity of Nitrates in Water and their removal, Dr. P. S. Fuller pp. 6 to 9.

"Pilot-Scale, High-Rate Biological Denitrification", John S. Jeris and Roger W. Owens, pp. 2043 to 2057 (1975).

Chemical Abstracts, vol. 88, No. 6 (2/1978), "Chemical Abstracts", p. 221.

Chemical Abstracts, vol. 98, No. 14 (4/1983), p. 348.

Primary Examiner—Tom Wyse
Attorney, Agent, or Firm—Poms, Smith, Lande & Rose

[57] ABSTRACT

The biological denitrification of water is improved in a decisive manner by reducing on the one hand the oxygen content of the water prior to passing it through the denitrification state and, on the other hand, by bringing the water into contact with the denitrification bacteria in a fluidized bed formed by sand the grains of which have been populated intentionally with denitrification bacteria of the species "pseudomonas fluorescens". Accordingly, the apparatus for carrying out the method comprises a stage (51) for eliminating oxygen preceding the denitrification reactor (52). If this stage is designed as a degassing stage, the reactor (52) is followed, advantageously, by a decarbonization stage (81).

7 Claims, 7 Drawing Sheets

METHOD FOR THE BIOLOGICAL DENITRIFICATION OF WATER

This is a continuation of copending application Ser. No. 06/912,545 filed on Sept. 29, 1986, now abandoned.

The present invention relates to a method for the biological denitrification of water, in particular for treating drinking water, using a denitrification stage comprising a base material with denitrification bacteria established thereon, including the steps of mixing the water to be treated with nutrients for the denitrification bacteria and passing the water thereafter through the denitrification stage.

In view of the increasing contamination of underground and surface water with nitrates, the denitrification of drinking water is gaining ever greater importance. Apart from ion exchange and reverse osmosis, biological denitrification is one of the methods that can be used for this purpose. Although it was developed originally for the treatment of sewage water, it lends itself also for the treatment of drinking water.

The invention starts out from a process for the biological denitrification of water as described by Haberer in the DVGW series of publications "Water" No. 31, Eschborn 1982, pages 147 to 162, in particular pages 152 et seq.

In water treatment, the process costs are very important because the water volumes to be denitrified are always very considerable and it is desired not to spend much money on the treatment of sewage water while, on the other hand, the cost of drinking water also should not be increased considerably by the treatment expenses. In the case of the known denitrification methods, the costs of the nutrients to be used for nourishing the bacteria are an important factor. The nutrients used include, for example, alcohols, molasses, or the like. In addition, the time required until a denitrification stage reaches its full effectiveness after start-up of the process is also an important factor. The length of this time is of particular importance where the denitrification stage has to be shut down at shorter intervals in order to clear the water passages that have been blocked by the continuous growth of the biomass.

Now, it is the object of the present invention to improve a method of the before-described type in such a manner that on the one hand reduced quantities of nutrients are sufficient to nourish the bacteria while, on the other hand, the process conditions are improved with a view to lowering the operating costs.

According to the invention, this object is achieved by the fact that the oxygen content of the water is reduced prior to passing the water through the denitrification stage.

Prior to splitting up the nitrate contained in the water in order to use up the oxygen linked to the nitrogen, the denitrification bacteria first use up the oxygen dissolved in the water. Accordingly, it was necessary heretofore to add a quantity of nutrients sufficient to enable the bacteria to use up the oxygen dissolved in the water. This same quantity of nutrients is saved by the method of the invention so that a corresponding reduction in operating costs is achieved.

In addition, considerable other advantages are derived from the reduction of the oxygen content in the raw water provided for by the invention. The fact that the oxygen content of the water has to be used up first leads to a multiplication of the bacteria which causes the biomass to grow excessively without, however, improving the denitrification effect. This phenomenon concerns in particular bacteria which are incapable of splitting up nitrate and which, therefore, impair the effectiveness of the biomass. Accordingly, when a reactor is started, it takes a long time until a sufficient quantity of denitrification bacteria are generated so that the full activity of the reactor is reached very slowly. In addition, that part of the biomass which does not assist the denitrification process, leads to premature blocking of the narrow apertures in the denitrification stage so that frequent interruptions of the operation, with the subsequent extended starting times, are required for cleaning. The frequency and duration of such interruptions are reduced by the reduction of the oxygen content according to the invention, and this contributes further towards rendering the process more economical.

Another advantage of the method of the invention lies in the reduction of the formation of undesirable nitrite which forms easily in the presence of oxygen dissolved in the water. Finally, carbon dioxide is produced by the bacteria from the added nutrient and the oxygen contained in the water, and this carbon dioxide also tends to impair the effectiveness of the denitrification process.

Another advantage of the method according to the invention lies in the fact that due to the introduction into the denitrification stage of water having a low oxygen content, there is no zone in which the oxygen contained in the water is used up initially so that the dimensions of the denitrification stage can be reduced by the size of this zone which would otherwise be required. This again helps increase the economy of the process.

The oxygen content in the water can be reduced in different ways. One variant of the method according to the invention provides, for example, that hydrogen is introduced into the water in the presence of a catalyst. This measure can be carried out very easily and leads to the formation of water from the oxygen contained in the water and the added hydrogen. Another equally simple method for reducing the oxygen content in the water consists in subjecting the water to a vacuum degassing process. This measure can also be carried out without considerable input as regards equipment and energy. Finally, the oxygen content of the water can be reduced also by introducing nitrogen into the water before the latter is passed through the denitrification stage so as to drive out the oxygen contained in the water and replace it by nitrogen. The nitrogen required for carrying out this embodiment of the method of the invention is available at low cost and can be introduced into the water under pressure in a simple manner. So, this embodiment does not give rise to any notable installation or operating expenses, except for the current consumption of nitrogen. In any case, it is possible to reduce the oxygen content of the water to a value as low as approximately 0.3 mg. $O_2$/liter. If the vacuum degassing method is applied, the pH value of the water and, under certain circumstances, also its temperature are increased a little, and this again has a favorable effect on the growth of the biomass and, consequently, the economy of the process.

According to another feature of the method of the invention, the bacteria strains *Pseudomonas fluorescens* DSM 3477 or DSM 3478 are used as denitrification bacteria, and phosphate $PO^{3-}$ is added additionally to the water. The addition of phosphate is necessary because it is an undispensable constituent of the cells of the bacteria. The before-mentioned strains are very effective as denitrification bacteria; they grow very well on the base material of a denitrification stage under conditions that can be easily monitored, and offer the additional advantage that they are non-pathogenic.

It has been found to be particularly advantageous for the performance of the method according to the invention if the nutrient added to the water is ethyl alcohol. In particular when the before-mentioned bacteria strains are employed, very effective denitrification is obtained which goes off according to the following formula:

$$7NO_3^- + 3{,}25 C_2H_5OH \rightarrow 3{,}5 N_2 + 6{,}5 CO_2 + 8{,}25 H_2O + 3OH^-$$

At the same time, the use of ethyl alcohol as a nutrient provides the advantage that ethyl alcohol is non-toxic and permits reliable after-cleaning.

In carrying out the method of the invention, the base material used for the denitrification bacteria may, advantageously, consist of sand having a grain size in the range of 0.3 to 1 mm., and the base material may be passed by the water in the denitrification stage from the bottom to the top at a velocity at which the base material forms a suspended or fluidized bed. Preferably, the sand used may be $SiO_2$ or garnet. Depending on the grain size and the specific gravity of the sand, but also on the degree in which the sand is covered by biomass, the flow velocity of the water may be in the range of 8 to 30 m/h.

The use of sand as a base material and of a suspended or fluidized bed offers the particular advantage to provide an extremely large surface for the growth of bacteria and to ensure in operation that the water to be treated gets into intimate contact with the bacteria established on the surface of the sand grains. This supports the effectiveness of the method of the invention quite considerably. The risk that the sand grains may cake together when the reactor containing the fluidized bed is shut down, or by excessive growth of the biomass, can be reduced if the base material is broken up by passing air through the sand intermittently, in particular before the process is started, but also during operation. In addition, it is also possible to stir the base material during operation of the reactor.

The time of contact between the water to be denitrified and the denitrification bacteria is determined by the size of the denitrification zone and the flow velocity of the water required for the proper operation of the process. If the contact time is insufficient to achieve the desired degree of denitrification, the water may be passed through several denitrification stages connected in series or else be recirculated from the outlet of the denitrification stage to its inlet in order to be passed several times through the same denitrification stage. By selecting appropriately the proportion of recirculated water relative to the raw water supplied into the system, it is possible to adjust practically any desired degree of denitrification. A high recirculation rate may be of advantage in particular during the starting phase of the process when the biomass and, accordingly, the degree of denitrification achievable by one passage through the denitrification stage is still low. In order to shorten the starting phase of the process, it is also possible to raise the water temperature to 15° to 20° C. during the starting phase.

The present invention further relates to an apparatus for carrying out the method described before. Known devices of this type, as described by the publication quoted before, comprise a reactor containing a base material with denitrification bacteria established thereon, and means for passing water through the reactor and for mixing nutrients into the water. According to the invention, the reactor is preceded by a device for eliminating the oxygen dissolved in the water. The device in question may consist, for example, of a vacuum degassing stage, a hydrogenizing stage, or a stage for introducing gaseous nitrogen. The use of a vacuum degassing stage provides the particular advantage of simple design and low operating costs. In addition, such a stage acts to reduce not only the oxygen content, but also the $CO_2$ content, while raising the pH value. Finally, the water is heated up to a certain degree in the vacuum degassing stage. Both factors, i.e. the rise of the pH value and of the water temperature, have a favorable effect on the denitrification process. A stage for introducing nitrogen comprises advantageously a vertical reaction vessel provided on its upper end with a water inlet and venting means and at its bottom with a water outlet and a distributor system for introducing gaseous nitrogen, Such a device offers an extremely simple design and does not require any operating input except for the nitrogen that is to be introduced, which is available at very low cost and which may be passed through the reaction vessel directly at the pressure prevailing in the commercially available nitrogen cylinders.

According to a preferred embodiment of the invention, the reactor is a suspended or fluidized-bed reactor designed as a vertical vessel containing a screen bottom with a sand filling having a grain size in the range of 0.3 to 1 mm arranged thereon, and comprising a supply line arranged below the said bottom and a discharge line for the treated water connected to its upper end. A reactor of this type is of simple design and permits at the same time the method of the invention to be carried out very efficiently.

Although it is of course possible to add the nutrients to the water to be treated in the area of the line leading to the reactor, it is particularly advantageous to use the space in the vessel below the screen bottom as a mixing chamber and to have the lines for the introduction of the nutrients arranged separately from the supply lines for the water and opening into the said space. The lines for the water and/or the nutrients may, conveniently, end in nozzles passing through the screen bottom and ensuring uniform distribution of the supplied liquid over the full cross-sectional areas of the vessel. The screen bottom may, for example, comprises a plurality of bores forming nozzles and having a length many times greater than their diameter and a diameter which is reduced at about the center of the said bores in the direction of flow. The nozzles may, however, also be provided in such a manner that the water to be denitrified and the nutrients are injected separately, at an angle of 70° to 90° relative to the axis of the vessel. According to a preferred embodiment of the invention, the nozzles connected with the nutrient lines are arranged above the nozzles connected with the water supply line so that the nutrients are taken up by the water, which is introduced in far greater quantities, and distributed over the whole vessel. The water nozzles may, for example, be provided with injection openings arranged in a star pattern, and the nutrient nozzles may be arranged in the middle between the injection openings of the water nozzles.

The supply of the water and of the nutrients can be effected in a particularly convenient manner when the space below the screen bottom is subdivided into two chambers by a wall extending in parallel to the screen bottom and when the water and nutrient supply lines, with their respective nozzles, are connected to one of these chambers, respectively.

In particular in cases where the reactor has a considerable height and where the water is loaded relatively heavily with nitrate so that a relatively low flow velocity of the water is required to ensure perfect denitrification, it may happen that the biomass existing in the reactor may grow so considerably that the particles of the base material stick together and the passages for the water are blocked. In such cases, the fluidized bed can be broken up by blowing in air. A preferred embodiment of the invention, therefore, provides that an air supply line is connected to the lower end of the vessel. By introducing air into the reactor intermittently during the starting phase, it is also possible to assist the initial whirling up of the base material. Likewise, it may be convenient to provide an agitator in the vessel to assist the discharge from the reactor of any detached biomass and of gases released in the course of the process, in particular nitrogen ($N_2$) and carbon dioxide ($CO_2$).

The invention will be described hereafter in greater detail with reference to the embodiments illustrated in the drawing in which FIGS. 1a, 1b show a diagrammatic representation of a first apparatus according to the invention;

FIG. 3 is a top view of one portion of the screen bottom of the reactor of the apparatus shown in FIG. 1a;

FIG. 7 shows a cross-section through the lower portion of the reactor of the apparatus according to FIG. 6a;

Figure 1A:
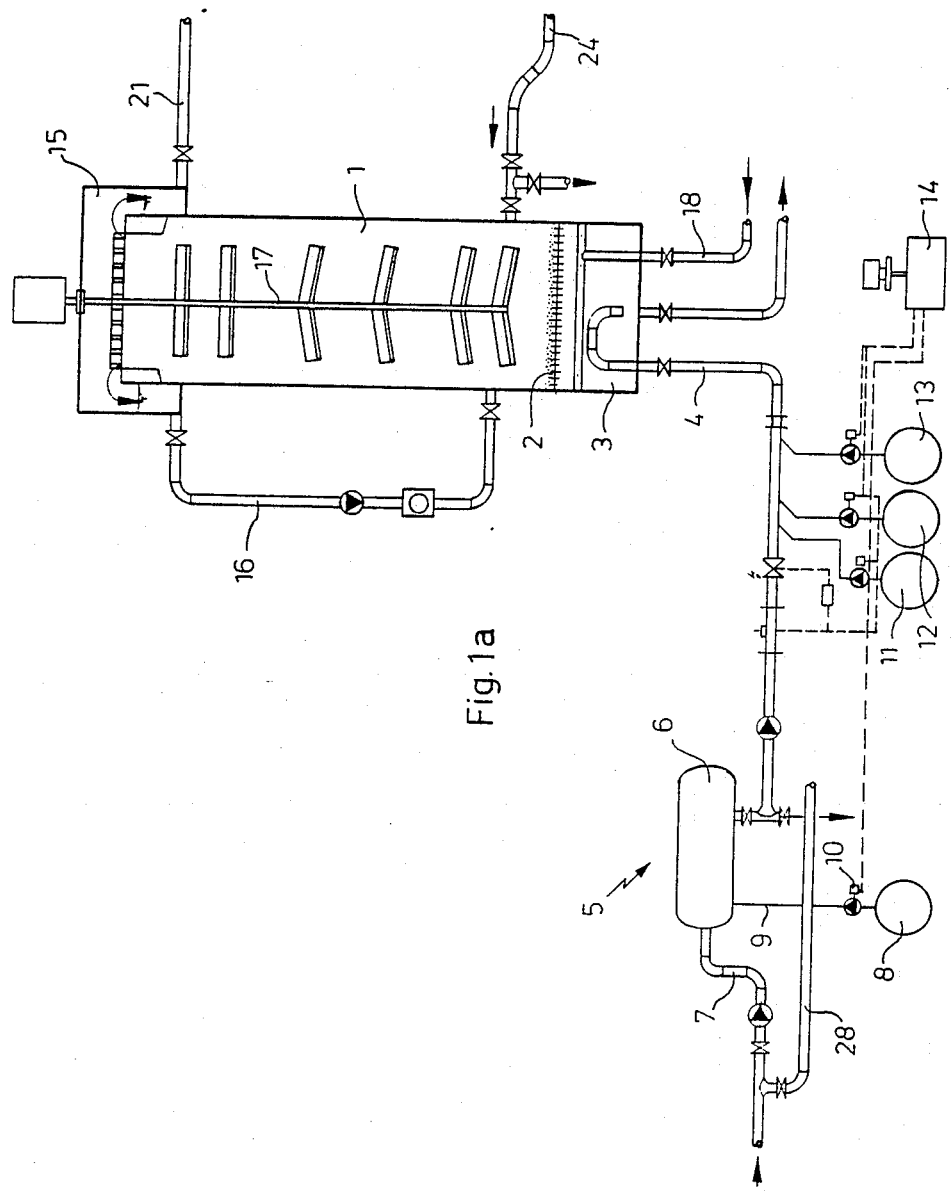
Figure 1B:
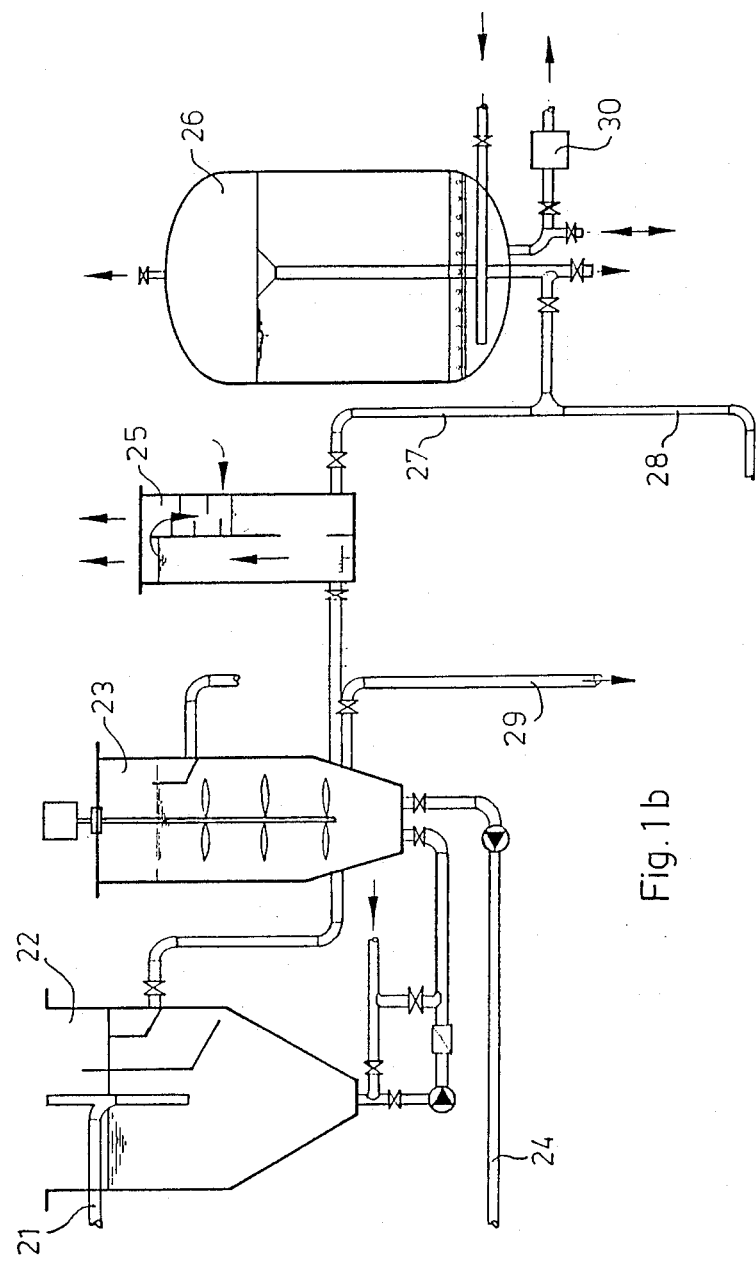

The apparatus for carrying out the method of the invention shown in FIGS. 1a, 1b consists mainly of a reactor 1 in the form of a cylindrical upright vessel comprising a sand filling—not shown in detail—with a grain size of 0.3 to 0.5 mm arranged on top of a screen bottom 2. The sand grains are populated with denitrification bacteria of the strains "*Pseudomonas fluorescens*" DSM 3477 and DSM 3478. A water supply line 4 arriving from a hydrogenizing stage 5 opens into the space 3 below the screen bottom 2. The hydrogenizing stage just mentioned comprises a tank 6 to which raw water is supplied via a line 7 and into which hydrogen is introduced, from a vessel 8 via a line 9 containing a controlled metering pump 10, in quantities stoichiometric to the oxygen dissolved in the raw water. The tank 6 contains a catalyst which causes the oxygen dissolved in the water to combine with the nitrogen to form water. Accordingly, the water leaving the hydrogenizing stage 5 and supplied to the reactor 1 via line 4 is substantially free from dissolved oxygen.

The line 4 is connected with vessels 11, 12, 13 permitting the reactants required for the operation of the process, in particular nutrients for the bacteria established in the reactor 1, to be added to the water being supplied to the reactor 1. The vessel 11 may, for example, contain ethyl alcohol, the vessel 12 may contain phosphate. The quantities introduced into the water in the line 4 are metered by a control unit 14.

The outlet of the reactor 1 is connected via a line 21 with a sedimentation tank 22 which is in turn followed by a washing tank 23. A line 24 leads from the washing tank 23 back to a point of the reactor 1 closely above the screen bottom 2. The apparatus according to FIGS. 1a, 1b comprises further a gas adsorption and degassing chamber 25 provided downstream of the washing tank and followed in turn by a multi-layer filter 26 and a degerminating stage 30. The line 27 connecting the gas adsorption and degassing chamber 25 and the multi-layer filter 26 is connected with the supply line 7 for the raw water via a line 28.

Figure 2:
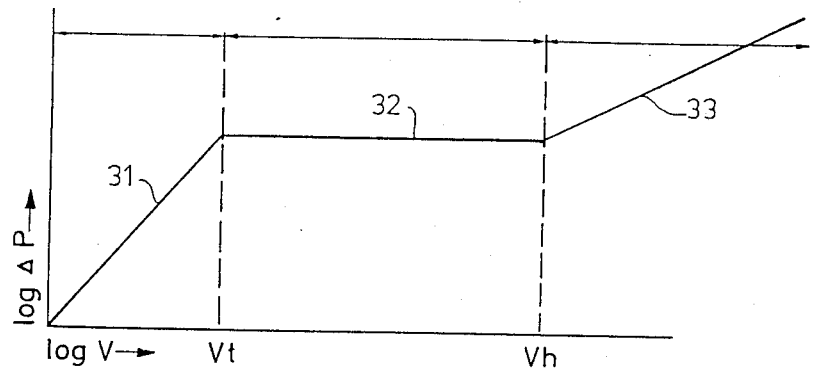
FIG. 2 shows a diagram illustrating the operation of a suspended/fluidized-bed reactor.

The reactor 1 is a suspended/fluidized-bed reactor which means that the water introduced via line 4 flows through the screen bottom 2 and the sand filling contained in the vessel 1 at a velocity sufficient to fluidize the sand bed. FIG. 2 shows a diagram illustrating the conditions existing in such a reactor, depending on the flow velocity of the water. The water velocity V has been plotted logarithmically on the abscissa, while the pressure $\Delta P$ prevailing above the bed formed by the sand contained in the tank has been plotted logarithmically on the ordinate. When the water flows at low velocities, the sand contained in the tank 1 will form a solid bed, which means that the sand grains occupy a firm position. As the flow velocity V rises, the pressure $\Delta P$ prevailing above the sand bed will increase, as shown by section 31 of the curve of FIG. 2. Once a given speed Vt has been reached, the solid bed assumes the condition of a fluidized bed, which means that the sand grains are entrained by the water flow, the flow velocity being just sufficient to break up the solid bed, but insufficient to entrain the sand grains and discharge them from the reactor. In the fluidized condition of the bed, the pressure $\Delta P$ prevailing above the bed remains constant, as shown by the curve section 32 in FIG. 2. However, when a given flow velocity Vh is reached, the sand grains of the bed are not only whirled up, but even entrained by the water flow. In this condition, a hydraulic discharge occurs which is accompanied by a further rise of the pressure $\Delta P$, as illustrated by the curve section 33 in FIG. 2. The reactor 1 is operated in the fluidized-bed condition represented by the section 32 of the curve. The flow velocity of the water is dependent on the grain size and the specific gravity of the sand contained in the vessel. In the case of the apparatus shown in the drawing, quartz sand having a grain size of 0.3 to 1 mm may be used, and the water flow may have a velocity of 8 to 30 m/h. However, garnet sand may also be used instead of quartz sand. The reactor may have a height of 3.5 to 5 m. As regards the grain size of the sand, the decisive factor lies in the fact that larger grains have a smaller surface so that they offer a smaller area for the establishment of denitrification bacteria. Consequently, the effectiveness of the populated fluidized bed increases as the grain size rises. At the same time, higher velocities are admissible and also required to achieve, while not to exceed, the fluidized-bed condition. One will therefore select the optimum grain size for a given size of the reactor vessel depending on the degree to which the water is loaded with nitrite and the desired throughput. The grain sizes preferably used are 0.3 to 0.5 mm, 0.4 to 0.6 mm and 0.5 to 0.8 mm.

The reactor 1 shown in FIG. 1a is provided on its upper end with a biomass trap 15 preventing larger quantities of biomass that may be discharged from the fluidized bed from being supplied to the sedimentation tank 14 via line 21. A return line 16 connects the trap 15 with a point of the tank closely above the screen bottom 2. In addition, an agitator 17 is provided in the reactor 1, and an air line 18 opens into the space 3 below the screen bottom 2.

Figure 3:
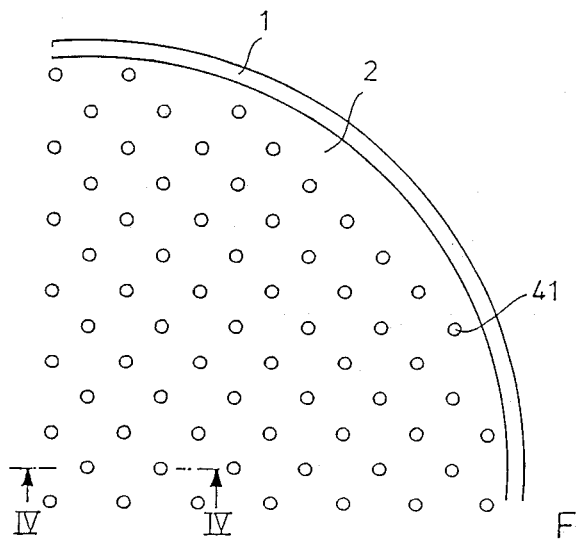
Figure 4:
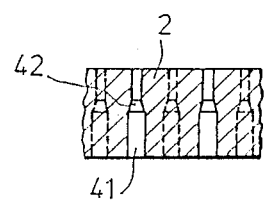
FIG. 4 shows a partial section through the screen bottom of FIG. 3, taken along line IV—IV.

To ensure proper operation of the reactor 1, it is important that the water which is supplied via line 4, mixed with nutrients for the bacteria, be distributed evenly over the whole cross-sectional area of the vessel to ensure that the sand bed is passed by the water and broken up uniformly and that the entire water flow gets into contact uniformly with the denitrification bacteria. The formation of passages in the form of channels during operation has to be avoided because these would permit the water to pass the sand bed rapidly in a concentrated current so that the desired reaction cannot take place. The screen bottom 2 of the reactor 1 shown in FIG. 1a, therefore, has the design of an aperture plate as illustrated in FIGS. 3 and 4, the thickness of the aperture plate being such that the length of the bores 41 is a multiple of their diameter. Moreover, the bores 41 are provided at about their center with a tapering portion 42 so that the diameter of the bores 41 is smaller at the upper outlet end than at the lower inlet end. In this manner, sort of nozzles are formed from which the water is ejected in a plurality of jets distributed over the whole cross-sectional area of the vessel 1 and which ensure that the sand bed is properly fluidized when the water is introduced at sufficiently high velocity. In the embodiment shown in FIGS. 3 and 4, the plate forming the screen bottom 2 has a thickness of 30 mm, while the bores 41 have diameters of 6 and 4 mm. Their spacing is 25 mm in the cross-sectional representation of FIG. 4.

During operation of the apparatus illustrated in FIGS. 1a, 1b, the raw water is supplied via line 7 to the hydrogenizing stage where the oxygen dissolved in the water is caused to react with the hydrogen introduced from the vessel 8 to form water. It is possible in this manner to reduce the normal oxygen content of the water, which is approximately in the range of 10 mg $O_2$/liter of water, to a value of approximately 0.3 mg/liter. After practically all oxygen has been removed from the water in this manner, the water is supplied via line 4 to the chamber 3 of the reactor below the screen bottom 2. During this process, the water is enriched, from the vessels 11 and 12, with nutrients for the denitrification bacteria contained in the reactor, i.e. ethyl alcohol and phosphate, which are introduced in quantities determined by the control unit 14. The water then flows upwards in the reactor 1, through the screen bottom 2, and gets into contact with the denitrification bacteria established on the sand grains in the fluidized bed. Given the fact that no oxygen is left in the water, the bacteria extract the oxygen needed by them for breathing from the nitrate contained in the water, thereby reducing the nitrate to gaseous nitrogen which is permitted to escape at the top of the reactor 1. The added ethyl alcohol and phosphate are used up during this process. Accordingly, the water leaving the reactor 1 via line 21 is substantially free from nitrate, and also free from any disturbing content of ethyl alcohol or phosphate. In a test setup, raw water containing between 55 and 75 mg $NO_3^-$/liter of water was passed through the reactor at a velocity of approximately 15 to 20 m/h whereby the nitrate content was reduced to values below 1 mg/liter.

The flow rate depends on the size of the sand grains and the degree in which the sand grains are covered by biomass. The higher the degree of coverage of the sand grains, the lower is the flow velocity of the water required for fluidizing the bed. An agitator 17 serves to stir the sand grains additionally and causes a certain amount of biomass to separate from the sand grains. Traces of biomass and sand are discharged from the reactor via line 21 and supplied to the sedimentation tank 22 and, thereafter, to the washing tank 23. Here, the water is separated from the sand and the biomass. The washed sand is circulated into the reactor 1 via line 24 whereas the separated biomass is discharged from the washing tank 23 as sludge through line 29.

The gas adsorption and degassing chamber 25, and the multilayer filter 26 connected downstream of the washing tank are stages of the type usual in the treatment of drinking water and intended to ensure the required quality of the drinking water.

The degree of denitrification achievable by the described apparatus, i.e. to a nitrate content of less than 1 mg/liter, is far better than required by the current Regulations. According to EEC standards, the limit value of nitrate for drinking water is 50 mg/liter. The guide value provides for a nitrate content of approximately 25 mg/liter. It is, therefore, possible to blend water that has been denitrified almost completely according to the process of the invention with raw water in order to bring the nitrate value up to a range between 20 and 25 mg nitrate/liter of water, for example.

When starting up the apparatus illustrated in FIGS. 1a and 1b, the vessel of the reactor 1 is filled with the required quantity of sand which is at that time not yet populated with bacteria. Instead of relying on the population of the sand bed with the denitrificants naturally encountered in water, it is provided according to the invention that the sand bed is mixed with a solution containing denitrification bacteria of the species "*pseudomonas fluorescens*" DSM 3477 and/or DSM 3478. The bacteria of the before-mentioned strains so introduced in large quantities will then multiply rapidly under the effect of the nutrients introduced with the water so that the apparatus will reach its full effectiveness very rapidly. It may be useful in this connection to circulate the water initially through the line 16 and to enrich it, if desired, with sodium nitrate from the vessel 13; however, the operation of the apparatus will start very quickly even if the water is introduced initially into the reactor at the minimum speed required for producing a suspended/fluidized bed. The formation of a suspended/fluidized bed may be assisted, in particular when the flow velocities are still low, by introducing compressed air through line 18, because compressed air acts to loosen up the sand forming the fluidized bed.

Given the fact that due to the removal of oxygen the bacteria live exclusively on the oxygen of the nitrate contained in the water, effective denitrification is obtained from the very beginning, and the bacteria adapt themselves also from the very beginning to the fact that they have to split up the nitrate to get their vitally necessary supply of oxygen. While observing the residual content of nitrate in the water leaving the reactor, one can then increase the flow velocity of the water gradually until the intended operating value is reached. Under the conditions described here, starting-up a reactor of the described apparatus will take only a few days. It is a particular advantage of the apparatus according to the invention that the reactor can be maintained in operation without interruption because if biomass is discharged together with sand grains, it is ensured that the activated, cleaned sand will be returned to the reactor. It appears from the above that the process according to the invention, carried out with the aid of the apparatus of the invention, provides a reliable possibility of denitrifying drinking water at low cost.

Figure 5:
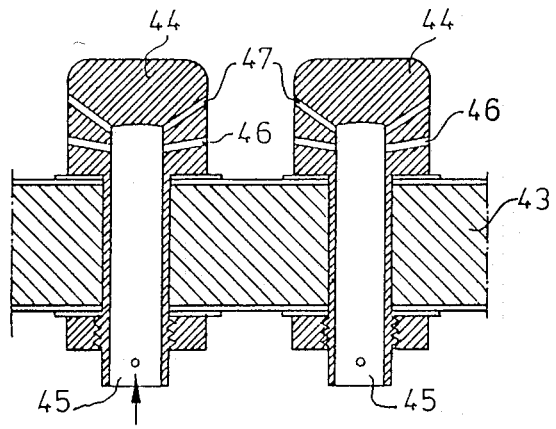
FIG. 5 shows a cross-sectional representation similar to that shown in FIG. 4, through another embodiment of a screen bottom.
Figure 7:
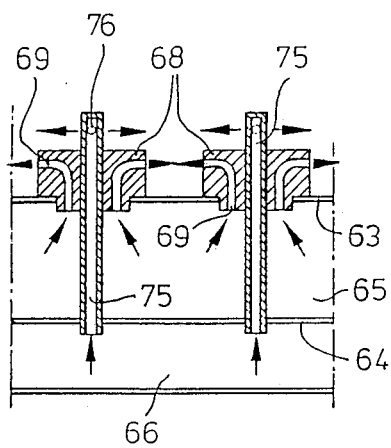

FIG. 5 shows a variant of a screen bottom 43 that can be substituted for the screen bottom 2 in the vessel forming the reactor 1 of the apparatus illustrated in FIGS. 1a, 1b. The screen bottom 43 consists again of a plate which is, however, not provided with a plurality of bores acting directly as nozzles, but rather with a lower number of larger bores with distributor nozzles 44 inserted therein. The distributor nozzles 44 comprise tubular sections 45 passing through the plate forming the screen bottom 43 and ending by their open ends in the space 3 of the reactor 1. At the sand-covered upper side of the screen plate 43, the distributor nozzles 44 are provided with heads passed by radial bores 46, 47 which extend right to the interior of the tubes 45, thus forming a connection to the space 3 of the reactor to which the water, which has been mixed with nutrients and which is to be denitrified, is supplied. The bores 46, 47 are distributed over the periphery of the nozzle heads in star-like pattern and ensure fine distribution of the incoming water over the whole cross-sectional area of the reactor.

The embodiment shown in FIGS. 6a and 6b comprises again a stage 51 for the elimination of oxygen, a reactor 52 containing a sand bed populated with denitrification bacteria, a sedimentation tank or solid-matter trap 53 provided downstream of the reactor 52, a washing tank 54, a gas adsorption and degassing chamber 55, a multilayer filter 56 and a degerminating stage 57. The apparatus is insofar identical to the apparatus shown in FIGS. 1a and 1b. Contrary to the apparatus described before, the means for eliminating the oxygen is designed in this case as a two-stage vacuum degassing system. The water is in this case atomized in the first stage 61 and then irrigated in the second stage 62 over suitable installations. Both stages operate at a vacuum so that almost complete degassing of the water is achieved. Here, too, the oxygen content is lowered from the saturation value of approximately 10 mg $O_2$/liter to approximately 0.3 mg $O_2$/liter. Simultaneously, the free carbon dioxide is eliminated whereby the pH value of the water increases. In addition, a temperature rise of the water can be observed which has a favorable effect on the subsequent denitrification process.

Another feature by which this embodiment distinguishes itself from the apparatus illustrated in FIGS. 1a, 1b lies in the fact that the space below the screen bottom 63 is subdivided into two chambers 65, 66 by a wall 64 extending in parallel to the screen bottom. The water leaving the vacuum degassing state 51 is supplied directly into the upper chamber 65 of the rector 52 from where it is passes into the reactor space filled with sand through nozzles 68 inserted in the screen bottom 63. The nozzles 68 are provided with channels 69 whose ends open in a position parallel to the screen bottom 63 in the rector 52 so as to ensure uniform distribution of the water in a star-like pattern.

A partial stream of the water leaving the degassing stage 51 is branched off via line 70 and supplied to the lower chamber 66 of the reactor 52. This comparatively small quantity of water is mixed with ethyl alcohol and phosphate from the vessels 71, 72, 73, which is added in quantities controlled by a control means 54 and intended as nutrients for the bacteria. If desired, a certain quantity of sodium nitrate may also be added during the starting phase of the apparatus. From the lower chamber 66, the nutrient solution supplied via line 70 is then also introduced into the reaction space of the reactor 52 through additional nozzles 75. These additional nozzles 75 consist substantially of tubes whose open ends extend right into the chamber 66 and whose ends carrying injection openings 76 are passed through the nozzles 68. Accordingly, the nozzles 75 which are connected with the nutrient line are arranged above the nozzles 68 which are connected with the water supply line and provided with injection nozzles arranged in a star-like pattern and surrounding the nutrient nozzles 75 arranged at their center.

Figure 6A:
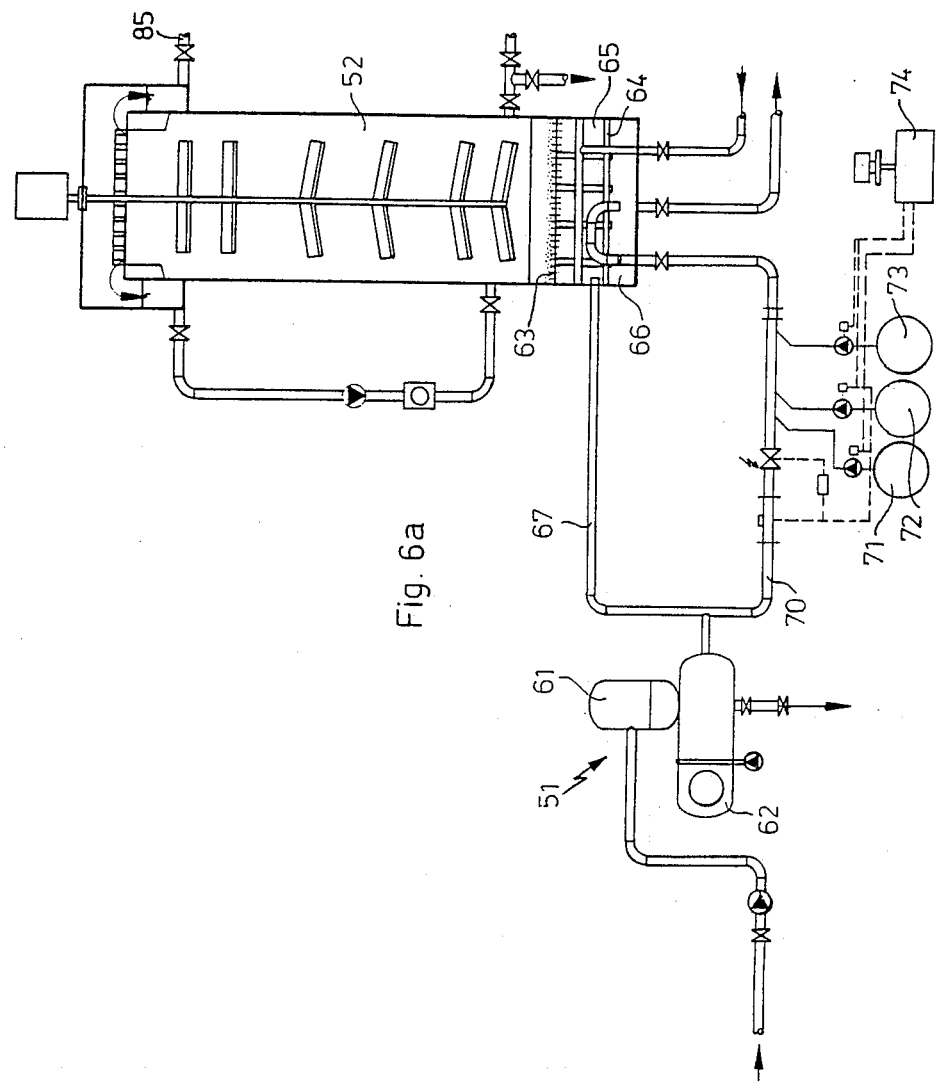
FIGS. 6a, 6b show a diagrammatic representation of another embodiment of an apparatus for carrying out the method according to the invention.
Figure 6:
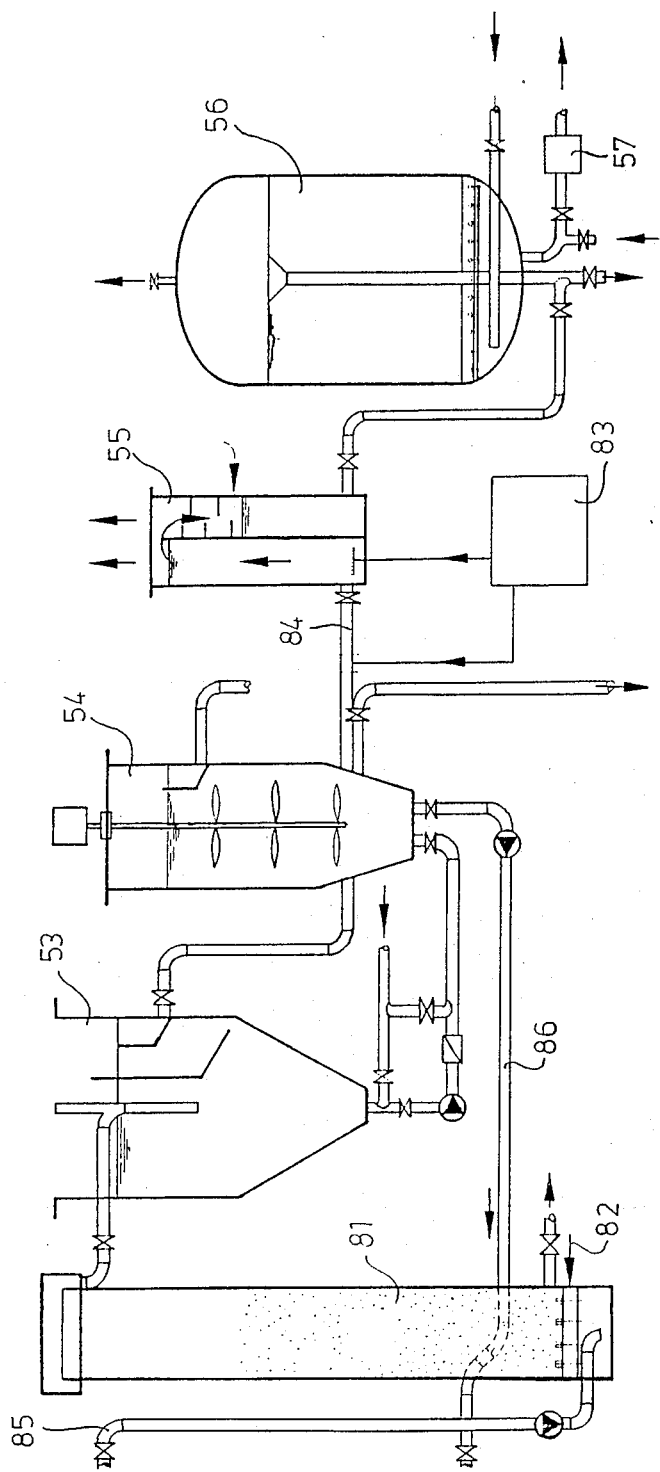

A remarkable particularity of the apparatus shown in FIGS. 6a and 6b is also seen in the fact that a decarbonization reactor 81 is arranged between the reactor 52 and the sedimentation tank 53. As mentioned before, the water has been degassed, whereby not only the dissolved oxygen, but also $CO_2$ has been eliminated. The removal of the carbon dioxide leads to an increase of the pH value which is advantageous not only for the denitrification process but also for the decarbonization process. The latter is effected by introduction of a basic substance through an inlet 82 provided at the lower end of the reactor 81. The basic substance used may consist, in particular, of milk of lime, soda or caustic soda. While the reduction of the carbonate hardness of the water is of considerable importance in the case of hard and very hard water, the residues of milk of lime or sodium remaining in the treated water are likewise disadvantageous so that in cases where milk of lime is added, one normally has to subject the water to a subsequent after-treatment the cost of which rise in proportion to the degree to which the water is loaded with these substances.

In addition, the substances added are also rather costly. The rise of the pH value of the water achieved by the process according to the invention permits the quantities of basic substances required, and the difficulties connected with the use of these substances, to be reduced quite considerably. It is, therefore, particularly advantageous to arrange the decarbonization reactor 81 downstream of the denitrification reactor 52 where the high pH value of the water is still maintained.

Finally, the apparatus shown in FIGS. 6a, 6b comprises in addition an ozonizing stage 83 operating in combination with the gas adsorption and degassing chamber, from which ozone is introduced into the line 84 interconnecting the washing tank 54 and the gas adsorption and degassing chamber 55, while air is introduced into the gas adsorption and degassing chamber 55. The almost complete elimination of gas from the water effected at the beginning of the process requires particularly careful introduction of gas and enrichment of the water with oxygen if the water is to be given the quality of drinking water.

Figure 8:
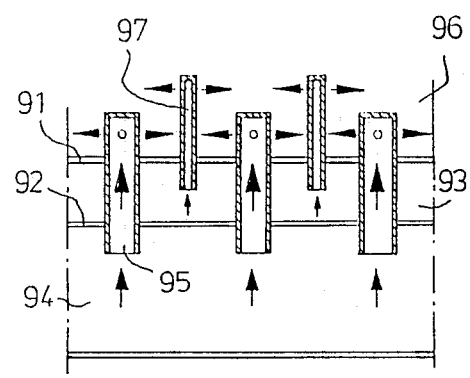
FIG. 8 shows another embodiment of the lower portion of a reactor, similar to that shown in FIG. 7.

FIG. 8 shows a variant of the design of the lower portion of the denitrification reactor 52. Although here again the space below the screen bottom 91 is subdivided into two chambers 93, 94 by a wall 92 extending in parallel to the screen bottom 91, the lower chamber 94 forms in this case a water chamber from which nozzles 95 project through the wall 92 and the screen bottom 91 into the reaction space 96 of the reactor, while nutrient nozzles 97 project from the upper chamber 92 through the screen bottom 91. The water nozzles 95 and the nutrient nozzles 97 are provided in this case in alternate arrangement, according to a pre-determined pattern. The nutrient nozzles 97 project beyond the screen bottom 91 a greater distance than the water nozzles 95. The outlet openings of both nozzle types are provided in horizontal arrangement so that the water to be denitrified is distributed over the cross-sectional area of the reaction space 96 at a lower level than the nutrient introduced through the nozzles 97. Accordingly, nutrients that have been distributed at a higher level are entrained by the rising water so that effective mixing of the nutrients and the water is achieved.

As mentioned before, the denitrification bacteria used in the method according to the invention belong to the strains "Pseudomonas fluorescens" DSM 3477 and/or DSM 3478. These bacteria strains distinguish themselves by particularly high effectiveness for the purposes of denitrification, good resistance and growth properties. It is of particular importance in this connection that these bacteria strains are non-pathogenic so that their use in drinking water does not present any problems.

The before-mentioned bacteria were produced by circulating underground water through the reactor at rising temperatures and with the addition of nutrients. This caused certain bacteria contained in the water to establish themselves, and gradually a denitrification process was initiated. The process was then continued with the addition of rising proportions of fresh raw water mixed with nutrients until the sand bed was closely covered with biomass and a substantially constant denitrification effect could be observed. When investigating the biomass, different strains of bacteria were found which all belonged to the species "Pseudomonas fluorescens". Of the bacteria obtained in the manner described before, two strains were isolated and deposited with the German Collection of Microorganism; they were assigned the numbers DSM 3477 and DSM 3478.

Now, in the case of the method according to the invention it is no longer a matter of chance what bacteria establish on the base materials of the denitrification reactor; rather, the base materials are inoculated with denitrification bacteria of the strains "Pseudomonas fluorescens" DSM 3477 and/or DSM 3478, preferably with a mixture of these strains, so that there are from the very beginning large quantities of denitrification bacteria which develop optimally under the conditions prevailing during the denitrification of drinking water, leaving accordingly little room for the development of other bacteria. Consequently, the best possible results are achieved by the method according to the invention under optimum conditions.

Figures 9, 10:
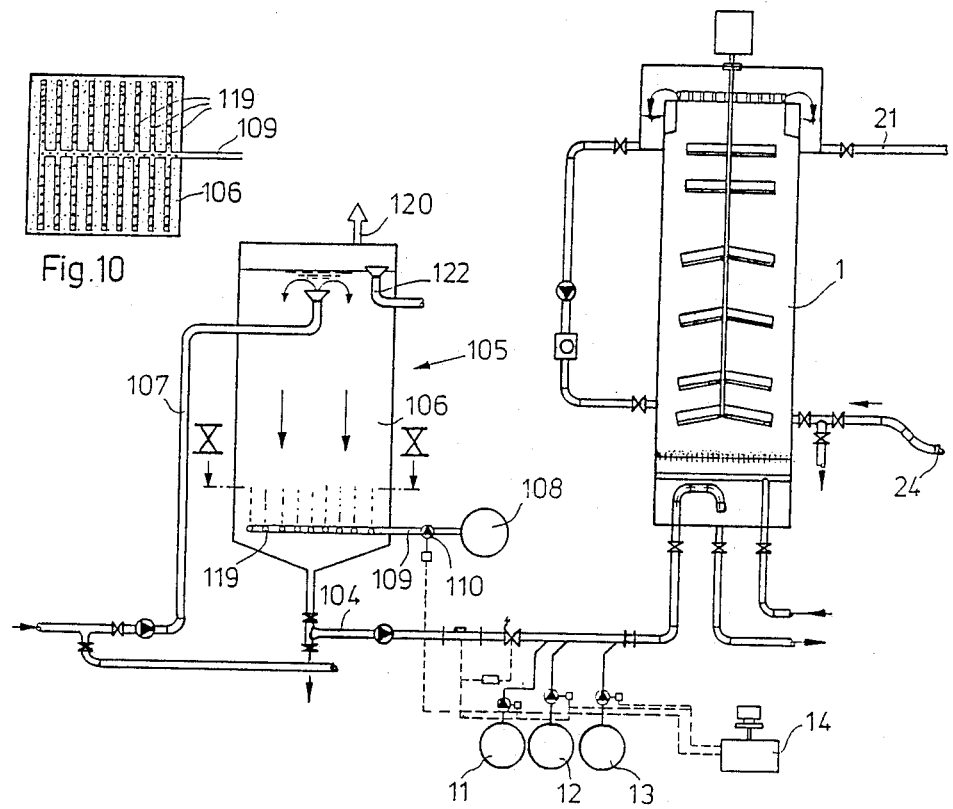
FIG. 9 is a diagrammatic representation of another apparatus according to the invention.
FIG. 10 shows a section through the reaction vessel of the apparatus according to FIG. 9, taken along line X—X.

The embodiment of the invention shown in FIGS. 9 and 10 differs from the embodiments described before only by the design of the device 105 for reducing the content of oxygen dissolved in the water. This device comprises a reaction vessel 106 to which raw water is supplied at its upper end via a line 107 and nitrogen ($N_2$) is supplied from a tank 108 via a line 109 and a controlled valve 110. The water introduced through the upper end of the reaction vessel 106 leaves the reaction vessel at its lower end through a line 104. The water, therefore, flows through the vessel 106 from the top to the bottom while the nitrogen entering the vessel 106 at the bottom passes through the water in the opposite direction, from the bottom to the top. A distributor system 116 arranged in the vessel 106 and connected to the line 109 ensures that the nitrogen is distributed evenly over the full cross-section of the water flowing through the reaction vessel 106. The nitrogen, which is introduced under pressure, expels the oxygen dissolved in the water under lower partial pressure. The expelled oxygen is permitted to leave the reaction vessel 106 at its upper end through a vent 120. An overflow pipe 122 ensures that a maximum water level is maintained in the reaction vessel 106.

Otherwise, the design of the arrangement is identical with the devices described before. This applies also to the vessels 11, 12, 13 connected to the water line 104, to the associated control unit 14 for the addition of nutrients to the water, to the arrangements provided downstream of the denitrification reactor 1 and connected to the latter via lines 21 and 24, and last not least to the design of the denitrification reactor 1 as such.

It goes without saying that the invention is not limited to the embodiments of the method and the apparatus described by way of example, but that deviations are possible without leaving the scope of the invention. In particular, the process parameters and the details of the apparatus may be varied to adapt them optimally to the properties of the raw water to be treated, the required quality of the treated water and also to the required throughput. In any case, however, it is of fundamental importance that the oxygen be eliminated from the water to be treated before bringing it into contact with the denitrification bacteria. In addition, the use of denitrification bacteria of the strains "Pseudomonas fluorescens" DSM 3477 and/or DSM 3478 and, in particular, the establishment of cultivated bacteria of this species on a fresh suspended/fluidize bed, are of particular importance for the high efficiency of the method.

We claim:

1. Method using a denitrification stage comprising a base material with denitrification heterotrophic bacteria established thereon, including the steps of mixing drinking water to be treated with nutrients for the denitrification bacteria and passing the water thereafter through the denitrification state, wherein the oxygen content of the water is reduced by a vacuum-degassing-process prior to passing the water through the denitrification stage.

2. Method according to claim 1, wherein the bacteria strains Pseudomonas fluorescens DSM 3477 or DSM 3478 are used as denitrification bacteria, and phosphate ($PO_4^{--}$) is added to the water.

3. Method according to claim 1, wherein the nutrient added to the water comprises ethyl alcohol.

4. Method according to claim 1, wherein the base material used for the denitrification bacteria comprises sand having a grain size in the range of 0.3 to 1 mm, and the base material is passed by the water in the denitrification stage from the bottom to the top at a velocity at which the base material forms a suspended or fluidized bed.

5. Method according to claim 4, wherein the flow velocity of the water is in the range of 8 to 30 m/h.

6. Method according to claim 4, wherein the base material is broken up by passing air through the sand.

7. Method according to any of claims 4, wherein the base material is stirred.

* * * * *